United States Patent [19]

Schonauer et al.

[11] Patent Number: 5,730,543
[45] Date of Patent: Mar. 24, 1998

[54] ELECTRICALLY CONDUCTING CONNECTION

[75] Inventors: Ulrich Schonauer, Karlsruhe; Michael Tafferner, Malsch; Hagen Fischer, Karlsruhe, all of Germany

[73] Assignee: Roth-Technik GmbH & Co. Forschung Fur Automobil-Und Umwelttechnik, Gaggenau, Germany

[21] Appl. No.: 669,364

[22] PCT Filed: Dec. 23, 1994

[86] PCT No.: PCT/EP94/04297

§ 371 Date: Aug. 2, 1996

§ 102(e) Date: Aug. 2, 1996

[87] PCT Pub. No.: WO95/18777

PCT Pub. Date: Jul. 13, 1995

[30] Foreign Application Priority Data

Jan. 5, 1994 [DE] Germany ............... 44 00 220.3

[51] Int. Cl.⁶ ............... C04B 41/90; C04B 37/02; H01R 43/02; H01R 4/02
[52] U.S. Cl. ............... 403/270; 403/179; 65/59.1; 65/59.3
[58] Field of Search ............... 29/877–880; 219/121.63, 219/121.64; 65/42, 59.1, 59.3; 403/179, 404, 270; 264/497

[56] References Cited

U.S. PATENT DOCUMENTS

| | | |
|---|---|---|
| 2,996,401 | 8/1961 | Welch et al. ............... 65/59.3 X |
| 3,154,503 | 10/1964 | Janakirama-Rao et al. ......... 65/59.3 X |
| 3,442,647 | 5/1969 | Klasens ............... 65/59.3 X |
| 3,523,357 | 8/1970 | Meyer ............... 65/59.1 X |
| 4,547,652 | 10/1985 | Raising et al. . |
| 4,652,727 | 3/1987 | Hoshizaki et al. ............... 219/541 |
| 4,713,520 | 12/1987 | Van Nice et al. ............... 219/121.64 X |
| 4,723,862 | 2/1988 | Ito et al. ............... 403/404 X |
| 4,978,052 | 12/1990 | Fister et al. ............... 65/59.1 X |
| 5,023,147 | 6/1991 | Nakata et al. . |
| 5,108,025 | 4/1992 | Kang et al. ............... 403/404 X |
| 5,306,891 | 4/1994 | Fleming et al. ............... 219/121.64 |

FOREIGN PATENT DOCUMENTS

| | | |
|---|---|---|
| 113895 | 7/1984 | European Pat. Off. . |
| 277645 | 8/1988 | European Pat. Off. . |
| 1022957 | 1/1958 | Germany . |

*Primary Examiner*—Anthony Knight
*Attorney, Agent, or Firm*—Antonelli, Terry, Stout, & Kraus, LLP

[57] ABSTRACT

An electrically conductive connection is made between a metal connector and a metal layer applied and bonded by sintering to a ceramic substrate comprising glass and/or vitreous ceramic in small quantities. An adhesion-promoting layer having a glass and/or vitreous ceramic and metal particles is applied and bonded by fusion to the ceramic substrate. The metal layer with the sintered bond is then applied to the ceramic substrate and the connector is welded to the metal layer by laser welding.

20 Claims, 1 Drawing Sheet

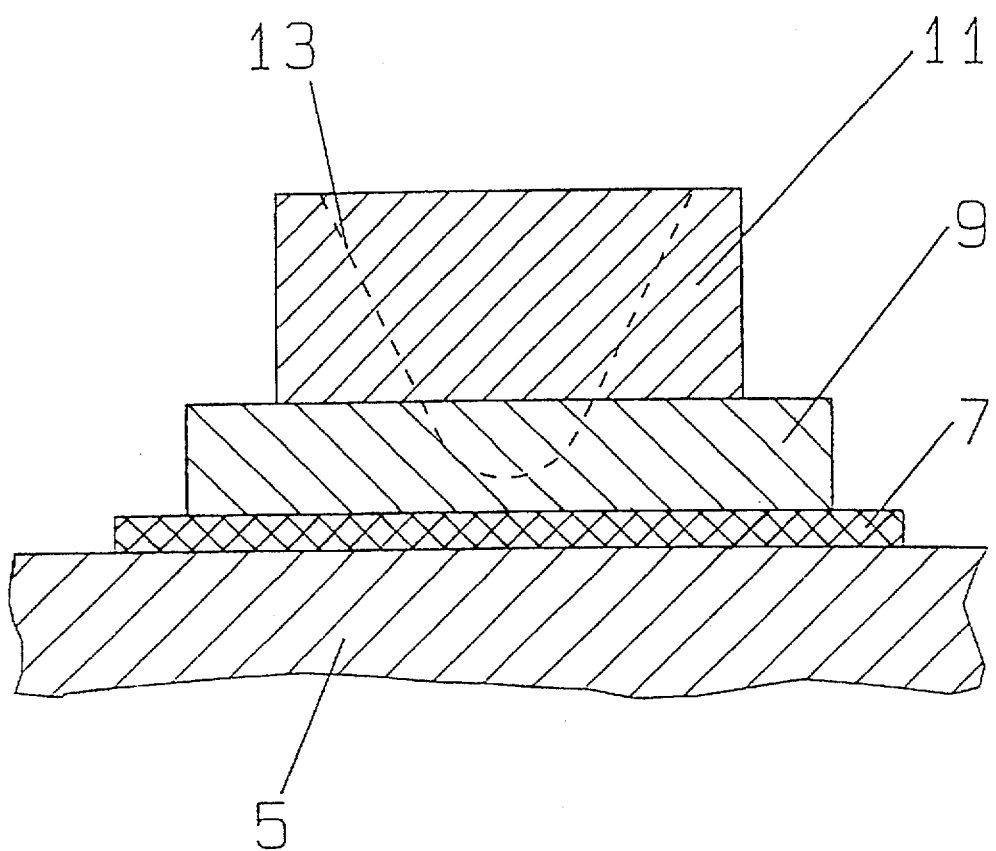

ELECTRICALLY CONDUCTING CONNECTION

The invention relates to an electrically conducting connection between a metal connector and a metal layer to which the connector is welded, said layer containing at least one metal and being mounted by a sintered connection on a ceramic substrate which preferably contains glass and/or glass ceramic in small quantities.

The type of connection described above has already been suggested for manufacturing.

However, such connections made in the laboratory have a number of disadvantages. Thus, the connection between the ceramic substrate and the metal, because of the very different properties of the materials of which the parts to be joined are made, especially their different coefficients of expansion and chemical compositions, is critical. Adhesion to the interface between the ceramic substrate on the one hand and the sintered metal layer on the other is extremely weak, firstly because the metal and ceramic form only a weak bond and secondly because the adhesion forces are very low. A sufficiently reliable connection cannot be ensured, particularly at high temperatures, and especially when mechanical stresses are added in addition, if welding is not performed on a sufficiently thick metal layer and/or a metallic connector, the metal layer and/or layers beneath, for example those of the ceramic substrate, are destroyed as a result, so that the electrical and/or mechanical system mounted on the ceramic substrate is no longer functional. In general, therefore, when producing the electrically conducting connection, either the reject rate is high or the electrical connection is not sufficiently mechanically stable and temperature-resistant.

The goal of the invention is to provide a connection as well as a method for the production of said connection that produce better and permanent connections.

In accordance with the teaching according to the invention, therefore, the metal layer is not applied directly to the ceramic substrate, but an adhesion-promoting layer is applied between these two layers, said adhesion-promoting layer containing glass and/or glass ceramic as well as metal particles in the form of flakes, powder, or the like to form a fused connection. A fused connection is produced between the glass and/or glass ceramic contained in the adhesion-promoting layer on the one hand and the glass components as well as the ceramic substrate or the latter alone on the other hand. Consequently, a positive connection is created between the ceramic substrate and the adhesion-promoting layer. At the same time, the metal particles of the adhesion-promoting layer join the glass components that melt or soften. As a result of this "flow," a positive connection is created between the various granular components and hence an intimate link results between the particles of the adhesion-promoting layer. Then the pure metal layer is applied to this adhesion-promoting layer, using thick-film technology for example, and joined to it by sintering. In this sintered connection, an intermetallic connection is formed between the metal particles of the metal layer and the metal particles in the adhesion-promoting layer. A mechanically strong bond with the adhesion-promoting layer is produced by a sintered connection. Then a metal connector in the form of a contact spring, contact clip, or metal foil is placed on the metal layer and is joined, especially advantageously because it takes place very quickly and with zero contact, by laser welding to form a good electrical connection with the metal layer that is mechanically extremely stable. When suitable high-temperature-resistant metals are used, noble metals such as platinum or their alloys for example, a high-temperature-resistant connection results that is a good electrical conductor and is mechanically extremely sturdy. It is especially suitable in highly oxidizing and corrosive environments at high temperature, in the hot and pulsating exhaust from internal combustion engines for example, as a connecting technique for gas sensors, lambda probes for example.

Surprisingly, it has also been found that the electrically conducting connection is mechanically so stable that it can simultaneously serve as a mechanical mount. Thus, in general, the result is a strong and permanent, electrically reliable connection that can be produced simply and economically with high reproducibility and processing safety during handling and manufacture. In addition, there is a cost-favorable integratability in the process and assembly process in which connections between two metals are already created by laser welding. In addition, laser welding offers the advantage of long service life. When suitable materials are chosen, noble metals for example, they can be used readily at high temperatures and in oxidizing as well as corrosive environments without the mechanical or electrical connection suffering as a consequence. The connection is formed especially advantageously when the metal of the metal layer and that of the metal particles of the adhesion-promoting layer are identical, in contrast to metals or their alloys that are only metallurgically similar or related.

Advantageous embodiments and improvements on the invention are characterized in the subclaims. One embodiment of the invention will now be described in greater detail with reference to the drawing showing a schematic cross section through a connection.

The ceramic substrate is labeled 5 and contains primarily $Al_2O_3$ with a small amount of glass and/or glass ceramic, approximately 4%. Adhesion-promoting layer 7 according to the invention is applied on top of said substrate by means of a fused connection. The adhesion-promoting layer contains metal particles in the form of flakes and/or powder or the like as well as glass and has a thickness of 7 to 8 μm in the finished product that includes all other layers.

The actual metal layer 9 is sintered over adhesion-promoting layer 7, said layer 9 containing in the initial state a metal, preferably a noble metal in particulate form, for example a powder, flakes, or the like. A metal connector 11, a clip or the like for example, is then placed on metal layer 9 and then connected with metal layer 9 by means of a laser spot weld. The area that is melted at this time is shown dashed and is labeled 13, and shows that not only the electrical connector, which is more than 100 μm thick, but also the metal layer that is about 40 to 60 μm thick (in the finished end product, with all other layers) is melted slightly areawise, as a result of which the intimate mechanical connection that is also a good electrical conductor is formed between connector 11 and metal layer 9 that leads to an electrical system on ceramic substrate 5. The laser weld also has the advantage that extremely small spots can be welded very accurately and with high reproducibility.

We claim:

1. Electrically conducting connection between a metal connector and a metal layer, said metal layer being applied by a sintered and/or melted connection and containing at least one metal, to which said metal connector is welded, characterized in that an adhesion-promoting layer containing glass and/or glass ceramic as well as metal particles is applied to a ceramic substrate and said metal layer is applied on top of said adhesion-promoting layer, and in that said metal connector is joined to said metal layer by means of a welded connection.

2. Connection according to claim 1 characterized in that said metal connector is joined with said metal layer by a laserwelded connection.

3. Connection according to claim 1 or 2 characterized in that said adhesion-promoting layer has a thickness of 5 to 15 μm, in the finished electrically conducting connection.

4. Connection according to claim 1, characterized in that said metal layer has a thickness of 20 to 100 μm in the finished electrically conducting connection.

5. Connection according to claim 1 characterized in that said adhesion-promoting layer, in its initial state, contains metal particles in the form of powdered metal and/or metal flakes.

6. Connection according to claim 1 characterized in that said metal connector is a foil, small plate, wire, or clip.

7. Connection according to claim 6 characterized in that the thickness of said metal connector is between 10 and 300 μm.

8. Connection according to claim 1 characterized in that said adhesion-promoting layer and/or said metal layer contains at least one noble metal.

9. Connection according to claim 1 characterized in that said metal connector is made of a corrosion resistant material.

10. Use of an electrically conducting connection according to claim 1 in the hot exhaust of an internal combustion engine as an electrical connection and/or mechanical fastening for a ceramic substrate of a gas sensor.

11. Method for manufacturing an electrically conducting connection between a metal connector and a metal layer, said metal layer being applied by a sintered connection and containing at least one metal, said metal layer further being mounted on a ceramic substrate containing glass and/or glass ceramic in small quantities, to which said metal connector is welded, characterized in that an adhesion promoting layer is applied using thick-film technology to said ceramic substrate and then sintered and/or melted, in that said metal layer is applied to said adhesion-promoting layer using thick-film technology and then sintered, and in that said metal connector is then welded onto said metal layer.

12. Method according to claim 11 characterized in that said metal layer is applied to said adhesion-promoting layer and the two layers are then sintered together.

13. Method according to claim 11 or 12 characterized in that said adhesion-promoting layer and/or said metal layer is/are applied as a thick layer using screen printing technology and/or masking technology.

14. Connection according to claim 1, wherein said metal layer also contains glass and/or ceramic in small amounts.

15. Connection according to claim 3, wherein said adhesion-promoting layer has a thickness of 7 to 12 μm in the finished electrically conducting connection.

16. Connection according to claim 4, wherein said metal layer has a thickness of 25 to 60 μm in the finished electrically conducting correction.

17. Connection according to claim 8, wherein said noble metal is platinum.

18. Use of an electrically conducting connection according to claim 10, wherein said gas sensor comprises a lambda probe.

19. A gas sensor in the hot exhaust of an internal combustion engine, said gas sensor comprising:

a ceramic substrate;

an adhesion-promoting layer, containing glass and/or glass ceramic as well as metal particles, applied to said ceramic substrate;

a metal layer applied on top of said adhesion-promoting layer by a sintered and/or melted connection and containing at least one metal; and a metal connector welded to said metal layer with an electrically conducting connection between said metal layer and said metal connector.

20. A gas sensor according to claim 19, wherein said gas sensor comprises a lambda probe.

* * * * *